United States Patent [19]
Lilley et al.

[11] Patent Number: 5,973,159
[45] Date of Patent: Oct. 26, 1999

[54] CHEMICAL PROCESS

[75] Inventors: Ian Andrew Lilley, Birkby; Raymond Vincent Heavon Jones, West Lothian; Stephen Martin Brown, Upper Cumberworth, all of United Kingdom

[73] Assignee: Zeneca Limited, United Kingdom

[21] Appl. No.: 09/027,930

[22] Filed: Feb. 23, 1998

[30] Foreign Application Priority Data

Mar. 7, 1997 [GB] United Kingdom .................... 9704795

[51] Int. Cl.$^6$ ...................... C07D 213/62; C07D 213/64
[52] U.S. Cl. ........................ 546/303; 546/301; 546/345
[58] Field of Search ...................... 546/301, 303

[56] References Cited

U.S. PATENT DOCUMENTS

| | | | |
|---|---|---|---|
| 3,355,456 | 11/1967 | Sexton | 331/87 |
| 3,609,158 | 9/1971 | Torba | 546/302 |
| 3,705,170 | 12/1972 | Torba | 546/291 |
| 3,787,420 | 1/1974 | Torba | 546/300 |
| 4,038,396 | 7/1977 | Shen et al. | 514/302 |
| 4,249,009 | 2/1981 | Bailey | 546/345 |
| 4,455,313 | 6/1984 | Ehr | 514/345 |
| 4,942,239 | 7/1990 | Orth et al. | 546/290 |

FOREIGN PATENT DOCUMENTS

| | | |
|---|---|---|
| 769015 | 12/1971 | Belgium . |
| 1075468 | 9/1987 | Japan . |
| 63-48268 | 2/1988 | Japan . |
| 288628 | 7/1929 | United Kingdom . |

OTHER PUBLICATIONS

Parker, Edwin D. and Shive, William; "Substituted 2–Picolines Derived from 6–Amino–2–picoline," *JACS*, 69, pp. 63–67 (1947).

Chemical Abstracts, 23, 607 (1929).

Klingsberg, Erwin, ed., *Pyridine and Its Derivatives*, Part Two, pp. 345–352, 408, 415 (1961).

Klingsberg, Erwin, ed., *Pyridine and Its Derivatives*, Part Three, pp. 571, 871 (1962).

*Primary Examiner*—Alan L. Rotman
*Attorney, Agent, or Firm*—Marian T. Thomson

[57] ABSTRACT

2-Hydroxy-6-trifluoromethylpyridine is prepared by reacting 2-chloro-6-trifluoromethylpyridine with an aqueous alkali metal hydroxide in a sealed vessel at a temperature of at least 140° C. under autogenous pressure.

6 Claims, No Drawings

CHEMICAL PROCESS

This invention relates to a chemical process and, more particularly, to a process for preparing 2-hydroxy-6-trifluoromethylpyridine which is useful in the manufacture of certain agricultural products.

Processes for preparing 2-hydroxypyridines by the hydrolysis of 2-chloropyridines are described in the chemical literature. Thus, UK Patent No. 288,628 describes the preparation of 2-hydroxypyridine by the hydrolysis 2-chloropyridine with solid potassium hydroxide at 175° C. It also describes the preparation of 2-hydroxy-5-nitropyridine by the hydrolysis of the corresponding chloropyridine with (a) concentrated hydrochloric acid in a bomb tube at 150° C. and (b) with 2-normal caustic soda lye under reflux.

U.S. Pat. No. 4,942,239 describes the preparation of 2-hydroxypyridine by the hydrolysis of 2-chloropyridine with an aqueous concentrated potassium hydroxide solution in the presence of a tertiary alcohol, such as tert-butyl or tert-amyl alcohol, under reflux at atmospheric pressure. A solvent-based process has also been described for the preparation of 2-hydroxy-6-trifluoromethylpyridine in, for example, U.S. Pat. No. 3,609,158. In this patent 2-chloro-6-trifluoromethyl pyridine in dimethylsulphoxide (DMSO) is hydrolysed by heating with aqueous sodium hydroxide under reflux.

2-Hydroxy-6-trifluoromethylpyridine can readily be prepared in good yield by the alkaline hydrolysis of 2-chloro-6-trifluoromethylpyridine in a solvent such as DMSO or tert-amyl alcohol. On a large scale, however, solvent-based processes are generally undesirable because of the environmental and safety implications and the need for solvent recovery systems.

Unfortunately, the treatment of 2-chloro-6-trifluoromethylpyridine with 35% hydrochloric acid at 150° C. results in only a trace of hydrolysis and with aqueous sodium hydroxide under reflux results in no hydrolysis at all. Treatment with solid base leads to hydrolysis but the product is obtained in an unacceptable physical form.

The process of the present invention is solvent-free, high yielding and provides the product in a suitable physical form.

Thus, according to the present invention, there is provided a process for the preparation of 2-hydroxy-6-trifluoromethylpyridine which comprises reacting 2-chloro-6-trifluoromethylpyridine with an aqueous alkali metal hydroxide in a sealed vessel at a temperature of at least 140° C. under autogenous pressure.

The alkali metal hydroxide is either sodium hydroxide or potassium hydroxide, the latter generally being the more effective. For maximum yield, the aqueous base solution strength should be at least 10% w/v and is suitably in the range of 10 to 50% w/v, for example, 10 to 20% w/v.

More than two equivalents of base are required to ensure fall conversion of the pyridine to pyridone. About 2.2 equivalents have been found generally satisfactory, based on pure pyridine starting material. A greater excess would appear unnecessary, while it may be possible to reduce the excess slightly. Thus, the normal working range will be from 2, preferably from 2.1, to 2.3 equivalents of base to pyridine starting material.

The temperature of the reaction should be at least 140° C. and is suitably 150° C.–160° C., typically 150° C. Below 150° C. the rate of hydrolysis is reduced.

The reaction is carried out in a sealed vessel, for example, in an autoclave whose material of construction can withstand the effects of aqueous alkali at temperatures of up to 150° C. and beyond and the autogenous pressures generated. Suitably the vessel is constructed from a nickel alloy such as inconel, monel or hastelloy. Normally pressures of 4 to 5 bar are generated.

In a typical small-scale process according to the present invention, 2-chloro-6-trifluoromethylpyridine is charged to an autoclave, which is sealed and pressure tested. The pressure is released, the autoclave resealed and heated to 150° C. At least two equivalents of aqueous alkali metal hydroxide are pumped to the autoclave and the reaction mixture held at 150° C.–160° C. over 1 to 4 hours, for example 1½ to 2 hours, under self-generated pressure of 4 to 5 bar. After reaction is adjudged complete, the reaction mixture is cooled, acidified and the product filtered and washed with water.

The 2-chloro-6-trifluoromethylpyridine starting material is a known compound and its preparation is described in the chemical literature. It may be prepared by the vapour phase chlorofluorination of α-picoline as described in EP-A-0042696 or by the fluorination of 2-chloro-6-trichloromethylpyridine (nitrapyrin) using hydrogen fluoride as described in EP-A-0110690 or using antimony trifluoro-dichloride as described in US-A-3682936.

The main advantage of the present invention is that it provides a high-yielding process for the hydrolysis of 2-chloro-6-trifluoromethylpyridine in the absence of a solvent. However, it has the additional advantage of being able to consume impure pyridine starting material and produce a 'cleaned-up' product. This is achieved by the hydrolysis of impurities in the feedstock to products having a higher water solubility than 2-hydroxy-6-trifluoromethylpyridine.

Commonly, 2-chloro-6-trifluoromethylpyridine feedstock contains impurities in which there is an additional chlorine atom in the 3- or 5-position of the pyridine ring. Some of these dichlorinated trifluoromethylpyridines are inseparable from 2-chloro-6-trifluro-methylpyridine by distillation. However, under the conditions of the present process, they are hydrolyzed to water-soluble hydroxypicolinic acid derivatives which are readily removed by acidification of the reaction mass and isolation of the precipitated product by filtration.

It should be noted, however, that additional base is required to hydrolyze these impurities. Four equivalents of base are needed for dichlorinated species. Therefore, the precise amount of base used in the process should be calculated according to the level of impurities in the feedstock.

The invention is illustrated by the following Examples in which:

```
       g = grammes
    mmol = millimoles
      ml = millilitre
   equiv = equivalent
     psi = pounds per square inch
     °C. = degrees centigrade
    HPLC = high performance liquid chromatography
```

EXAMPLE 1

This Example illustrates the preparation of 2-hydroxy-6-trifluoromethylpyridine by reacting 2-chloro-6-trifluoromethylpyridine with aqueous potassium hydroxide at 150° C. under autogenous pressure.

2-Chloro-6-trifluoromethylpyridine (10.0 g; 55.1 mmol; 1 equiv) was charged to a 100 ml Hastelloy C Parr reactor, the reactor sealed and pressure tested with nitrogen. When a sealed system had been achieved, the pressure was released, the reactor resealed, and heated to 150° C. Potassium hydroxide solution (10% strength; 68.0 g; 121.1 mmol; 2.2 equiv) was added via an HPLC pump over 1 hour, while the mixture was maintained at 150° C. Addition of base caused the pressure to rise to 5 bar. The reaction mixture was held at this temperature and pressure for a further 5 hours. Following this period the reactor was cooled, dismantled and sodium chloride (5 g) added. The solution was cooled to 5° C., acidified to pH 5–6 by the addition of concentrated sulphuric acid, filtered and pulled dry. The filter cake was washed with water (10 g), pulled dry, discharged and allowed to dry overnight to afford 2-hydroxy-6-trifluoromethylpyridine as a colourless powder (9.5 g; 95% strength; 92% isolated yield).

EXAMPLE 2

This Example illustrates the preparation of 2-hydroxy-6-trifluoromethylpyridine by reacting 2-chloro-6-trifluoromethylpyridine with aqueous sodium hydroxide at 150° C. under autogenous pressure.

2-Chloro-6-trifluoromethylpyridine (8.05 g at 98% strength; 43.2 mmol; 1 equiv) was charged to a Parr reactor, pressure tested at 100 psi. The pressure was released and the reactor heated to 150° C. Sodium hydroxide solution (9.823% strength; 40.1 g; 98.5 mmol; 2.28 equiv) was added via an HPLC pump over 2 hours 20 minutes and the reaction mixture maintained at 150° C. for a further 4 hours. The mixture was cooled, unreacted 2-chloro-6-trifluoromethylpyridine extracted with methylene chloride, and the aqueous phase acidified with hydrochloric acid and filtered to afford 2-hydroxy-6-trifluoromethylpyridine (5.615 g; 93% strength; 73% isolated yield). Further product was obtained by extraction of the filtrates with methylene chloride.

We claim:

1. A solvent-free process for the preparation of 2-hydroxy-6-trifluoromethylpyridine which comprises reacting 2-chloro-6-trifluoromethylpyridine with an aqueous alkali metal hydroxide in the absence of a solvent in a sealed vessel at a temperature of at least 140° C. under autogenous pressure.

2. A process according to claim 1 wherein the strength of the aqueous alkali metal hydroxide is in the range of 10% to 50% w/v.

3. A process according to claim 1 wherein the alkali metal hydroxide is potassium hydroxide.

4. A process according to claim 1 wherein the amount of alkali metal hydroxide used is in the range of from 2 to 2.3 equivalents of base to 2-chloro-6-trifluoromethylpyridine starting material.

5. A process according to claim 1 wherein the temperature is in the range of from 150° C. to 160° C.

6. 2-Hydroxy-6-trifluoromethylpyridine whenever prepared by a process according to claim 1.

* * * * *